(12) United States Patent
Kogure et al.

(10) Patent No.: US 11,832,932 B1
(45) Date of Patent: Dec. 5, 2023

(54) SCRATCHING DETECTION SYSTEM

(71) Applicant: NAOS, Aix en Provence (FR)

(72) Inventors: Takamasa Kogure, Tokyo (JP); Eitaro Kondo, Tokyo (JP)

(73) Assignee: NAOS, Aix en Provence (FR)

( * ) Notice: Subject to any disclaimer, the term of this patent is extended or adjusted under 35 U.S.C. 154(b) by 0 days.

(21) Appl. No.: 18/037,400

(22) PCT Filed: Nov. 20, 2020

(86) PCT No.: PCT/JP2020/043365
§ 371 (c)(1),
(2) Date: May 17, 2023

(87) PCT Pub. No.: WO2022/107304
PCT Pub. Date: May 27, 2022

(51) Int. Cl.
*A61B 5/11* (2006.01)
*A61B 5/00* (2006.01)

(52) U.S. Cl.
CPC ............ *A61B 5/1114* (2013.01); *A61B 5/742* (2013.01); *A61B 5/6825* (2013.01); *A61B 2562/028* (2013.01); *A61B 2562/0219* (2013.01)

(58) Field of Classification Search
None
See application file for complete search history.

(56) References Cited

U.S. PATENT DOCUMENTS 11,523,770 B2   12/2022  Ikoma
2018/0228427 A1*  8/2018  Ikoma .................. A61B 5/445
2019/0129508 A1   5/2019  Harrison et al.

FOREIGN PATENT DOCUMENTS

JP        2020507434 A      3/2020

OTHER PUBLICATIONS

A. Moreau et al., "Detection of Nocturnal Scratching Movements in Patients with Atopic Dermatitis Using Accelerometers and Recurrent Neural Networks," in IEEE Journal of Biomedical and Health Informatics, vol. 22, No. 4, pp. 1011-1018, Jul. 2018, (Year: 2017).*

* cited by examiner

*Primary Examiner* — Benjamin S Melhus
(74) *Attorney, Agent, or Firm* — FORGE IP, PLLC

(57) ABSTRACT

A scratching detection system includes a sensor and processor. The sensor is configured to detect acceleration corresponding to movement of a person's hand and is configured to output a first signal including a detected value corresponding to the acceleration in a first cycle. The processor is configured to acquire the first signal and to detect a scratching behavior of the person in a second cycle based on a plurality of parameters. The second cycle includes a plurality of the first cycles. The plurality of parameters includes a first occurrence count and a first consecutive count. The first occurrence count is a number of times an absolute value of the detected value exceeds a threshold value in the second cycle. The first consecutive count is a maximum value of a number of times that the absolute value of the detected value consecutively exceeds the threshold value in the second cycle.

11 Claims, 11 Drawing Sheets

SCRATCHING DETECTION SYSTEM

FIELD OF THE INVENTION

Embodiments of the invention relate to a scratching detection system.

BACKGROUND OF THE INVENTION

For example, there is a system that monitors itchiness of a patient by performing a movement measurement of the body of the patient. A more accurate measurement is desirable.

PATENT LITERATURE

PTL 1: Japanese Translation of PCT International Application Publication No. 2020-507434

SUMMARY OF THE INVENTION

Technical Problem

Embodiments provide a scratching detection system in which scratching behavior can be more accurately detected.

Solution to Problem

According to an embodiment, a scratching detection system includes a sensor, and a processor. The sensor is configured to detect an acceleration corresponding to a movement of a hand of a person and is configured to output a first signal including a detected value corresponding to the acceleration in a first cycle. The processor is configured to acquire the first signal and to detect a scratching behavior of the person in a second cycle based on a plurality of parameters. The second cycle includes a plurality of the first cycles. The plurality of parameters includes a first occurrence count and a first consecutive count. The first occurrence count is a number of times that an absolute value of the detected value exceeds a threshold value in the second cycle. The first consecutive count is a maximum value of a number of times that the absolute value of the detected value consecutively exceeds the threshold value in the second cycle.

Effects of the Invention

According to embodiments, a scratching detection system can be provided in which scratching behavior can be more accurately detected.

DETAILED DESCRIPTION OF THE INVENTION

Figure 1:
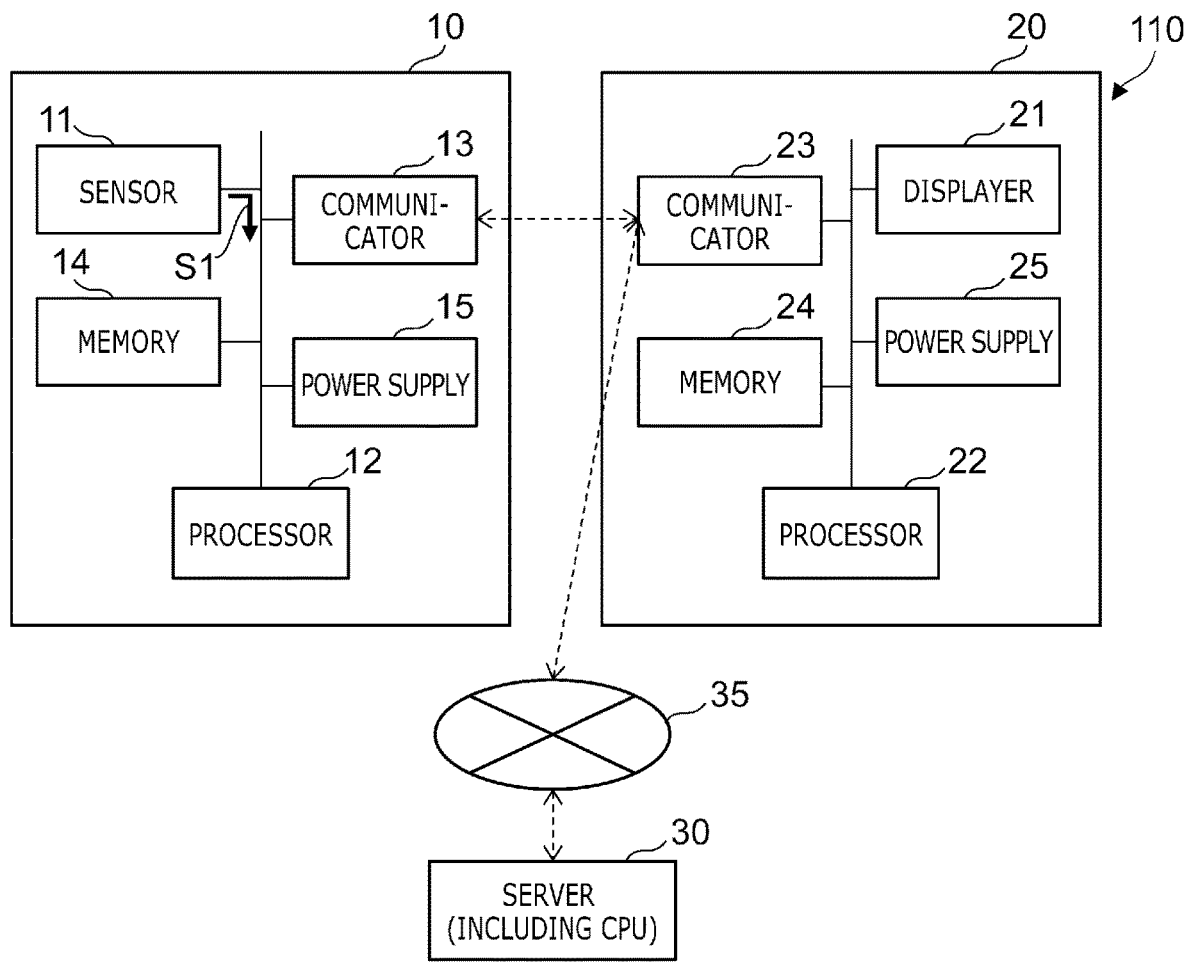
FIG. 1 is a schematic view illustrating a scratching detection system according to a first embodiment.

Various embodiments will be described hereinafter with reference to the accompanying drawings.

The drawings are schematic or conceptual. The size ratio between the portions is not necessarily identical to those in reality. Furthermore, the same portion may be shown with different dimensions or ratios in different figures.

In the present specification and drawings, the same elements as those described previously with reference to earlier figures are labeled with like reference numerals, and the detailed description thereof is omitted as appropriate.

First Embodiment

FIG. 1 is a schematic view illustrating a scratching detection system according to a first embodiment.

Figure 2A:
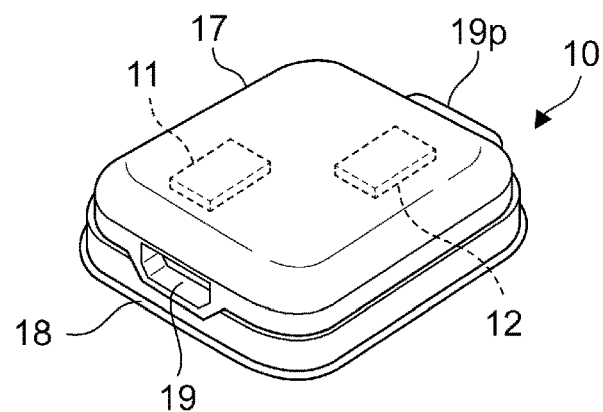
FIGS. 2A to 2C are schematic views illustrating the scratching detection system according to the first embodiment.
Figure 2B:
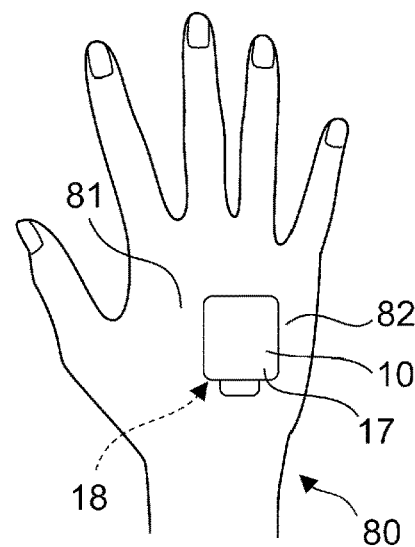
Figure 2C:
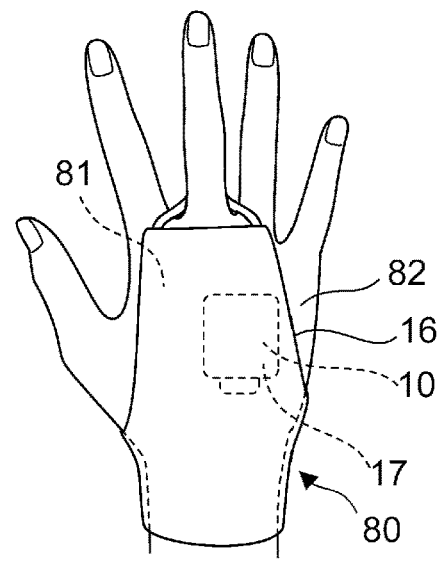

FIGS. 2A to 2C are schematic views illustrating the scratching detection system according to the first embodiment.

As shown in FIG. 1, the scratching detection system 110 according to the embodiment includes a measuring device 10. As described below, for example, the measuring device 10 is configured to detect whether a person is scratching a part of the body of the person. The person is a user of the scratching detection system 110, for example. The scratching detection system 110 can detect a scratching behavior of the person, that includes a scratching, a rubbing, a tapping and the like. The scratching detection system 110 may further include an output device 20.

As shown in FIG. 1, the measuring device 10 includes a sensor 11 and a processor 12. The measuring device 10 may include a communicator 13, a memory 14, a power supply 15. The output device 20 includes a display 21. The output device 20 may include a processor 22, a communicator 23, a memory 24, and a power supply 25.

The measuring device 10 and the output device 20 can communicate with each other. For example, the communicator 13 and the communicator 23 can communicate with each other. For example, the communicator 23 may be able to communicate with a server 30 via a network 35. The server 30 may include, for example, a processor such as a CPU, etc.

As described below, for example, in the measuring device 10, the sensor 11 is configured to detect the movement (e.g., the body movement) of the person. The processor 12 is configured to perform a determination operation (i.e., a first operation) to determine whether the person is scratching based on data received from the sensor 11 and generate the detection result. The detection result can be output to the output device 20 via the communicator 13. The detection result and a program or software relating to the processing of the processor 12 may be stored in the memory 14. The sensor 11, the processor 12, the communicator 13, and the memory 14 can be operated by power supplied from the power supply 15. The power supply may include, for example, a battery.

In the output device 20 as described below, the display 21 is configured to display information related to the detection result of the sensor 11. For example, the output device 20 acquires the information (e.g., signal) based on the detection result of the sensor 11 via the communicator 23. For example, the processor 22 may calculate information from the detection result. The information includes a period when the person is scratching during one night for example. The information in detail is described later. For example, the display 21 displays the information. For example, the memory 24 is configured to store the detection result acquired via the communicator 23, and the information calculated by the processor 22. The display 21, the processor 22, the communicator 23, and the memory 24 can be operated by power supplied from the power supply 25. The power supply 25 may include, for example, a battery. The output device 20 may include, for example, a portable terminal (e.g., a smartphone, etc.). Any wireless or wired communication method is applicable to the communication between the communicator 13 and the communicator 23.

As shown in FIG. 2A, in one example, the measuring device 10 may include a housing 17. The sensor 11, the processor 12, etc., may be provided in the housing 17. The communicator 13, the memory 14, the power supply 15, etc., are not illustrated in FIG. 2A. As shown in FIG. 2A, a power input terminal 19 (e.g., USB: universal serial bus) can be provided in the measuring device 10. As shown in FIG. 2A, the measuring device 10 may include an adhesive member 18. For example, the adhesive member 18 is provided on the bottom face of the housing 17. The adhesive member 18 may include, for example, a sheet-like adhesive material.

As shown in FIG. 2B, the measuring device 10 can be detachably fixed to a hand 81 of the person 80. For example, the housing 17 is fixed to the hand 81 by the adhesive member 18. As shown in FIG. 2A, a protrusion 19p can be provided in the housing 17. The person 80 can easily attach and release the housing 17 from the hand 81 by handling the protrusion 19p.

As shown in FIG. 2C, a glove-shaped member 16 may be provided in the measuring device 10. At least one finger of the person 80 can pass through a portion of the glove-shaped member 16, for example. The housing 17 is placed between the back 82 of the hand 81 and the glove-shaped member 16. The glove-shaped member 16 may fix the position of the housing 17 with respect to the hand 81. The measuring device 10 may be detachably fixed to the hand 81 by the glove-shaped member 16. In the example shown in FIG. 2C, the adhesive member 18 may not be provided.

For example, the measuring device 10 is fixed to a back 82 of the hand 81. By fixing the measuring device 10 to the back 82, the person 80 can perform any operation using the palm and fingers of the hand 81 without discomfort.

The sensor 11 is configured to detect an acceleration corresponding to the movement of the hand 81 of the person 80. The sensor 11 includes, for example, an acceleration sensor. The acceleration sensor includes, for example, an MEMS (Micro Electro Mechanical Systems) device.

As shown in FIG. 1, the sensor 11 is configured to detect the acceleration in a first cycle and output a first signal S1. The first signal S1 includes a detected value. The detected value corresponds to the movement of the hand 81. For example, the first signal S1 changes when the hand 81 moves. The detected value that is included in the first signal S1 changes according to the acceleration corresponding to the movement of the hand 81. The sensor 11 is configured to output the first signal S1 in the first cycle. The first cycle is, for example, the sampling cycle of the acceleration. The first cycle is, for example, not less than 5 ms and not more than 500 ms. The first cycle is defined by a timer provided in the processor 12 of the measuring device 10. The processor 12 may change a length of the first cycle.

As shown in FIG. 1, the first signal S1 is supplied to the processor 12. The processor 12 is configured to acquire the first signal S1.

The direction of the acceleration detected by the sensor 11 is arbitrary. The acceleration in any direction is represented as components along three axes. The detected value that is included in the first signal S1 includes a component along a first axis of the acceleration, a component along a second axis of the acceleration, and a component along a third axis of the acceleration. The second axis crosses the first axis. The third axis crosses a plane including the first and second axes. For example, the first axis is an X-axis direction, the second axis is a Y-axis direction, and the third axis is a Z-axis direction.

Thus, the detected value may include three values in accordance with the three axes. Then, considering the orientation of the acceleration, the detected value may be divided into following six components: a first component of one of positive or negative along the first axis, a second component of one of positive or negative along the second axis of the acceleration, a third component of one of positive or negative along the third axis of the acceleration, a fourth component of the other of positive or negative along the first axis of the acceleration, a fifth component of the other of positive or negative along the second axis of the acceleration, and a sixth component of the other of positive or negative along the third axis of the acceleration. The acceleration that is received by the sensor 11 according to the movement of the hand 81 can be represented by the magnitudes (the absolute values) of these six components. The three axes may be arbitrarily set in the sensor 11. For convenience of description hereinbelow, the first to third components are taken to be positive, and the fourth to sixth components are taken to be negative.

Figure 3A:
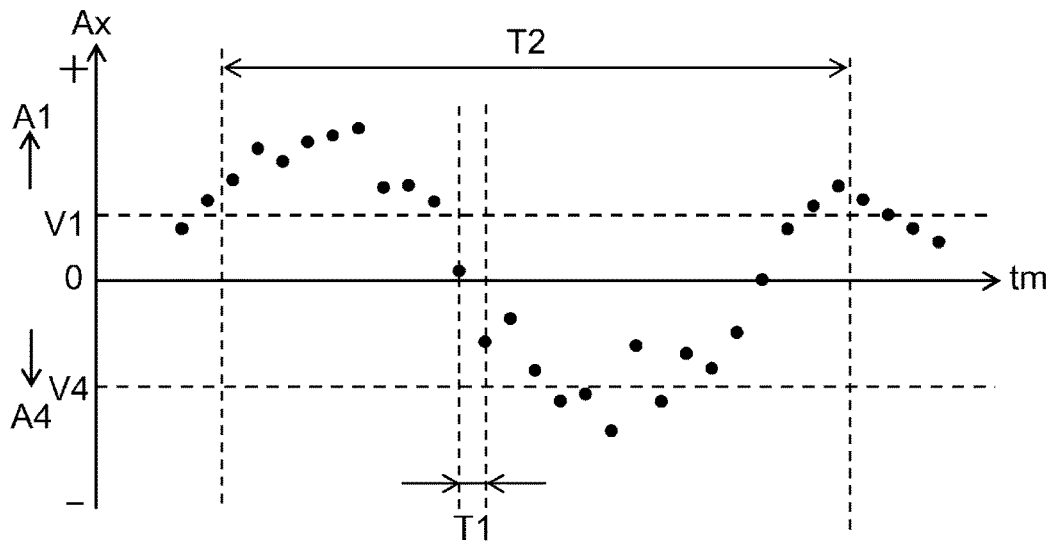
FIGS. 3A to 3C are schematic views illustrating a signal of the scratching detection system according to the first embodiment.
Figure 3B:
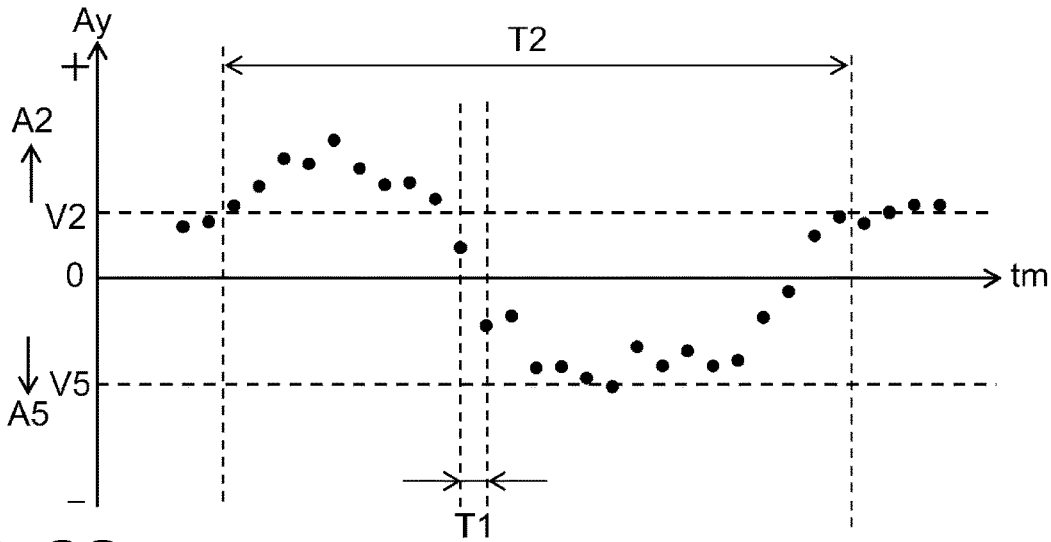
Figure 3C:
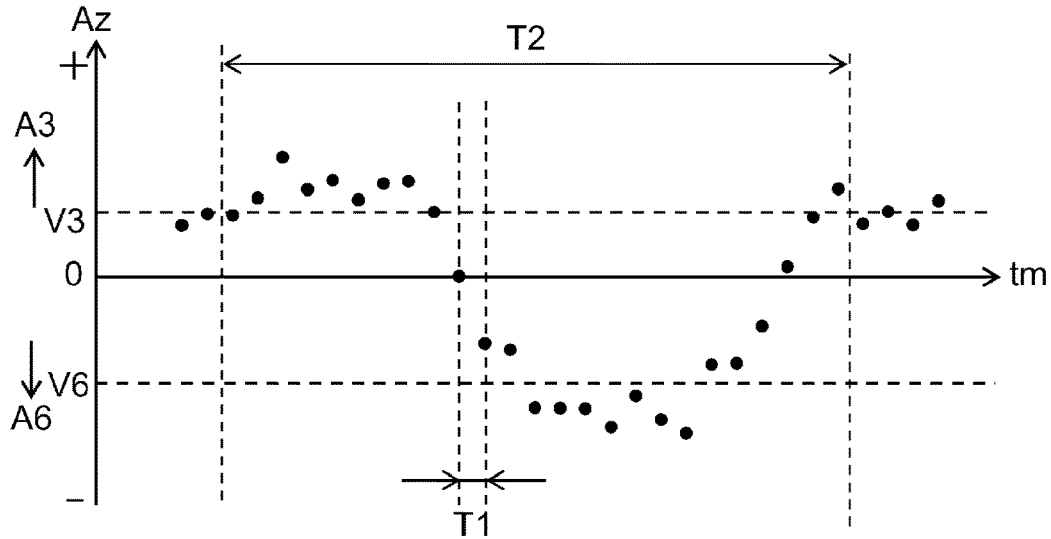

FIGS. 3A to 3C are schematic views illustrating a signal of the scratching detection system according to the first embodiment.

In these figures, the horizontal axis is a time tm. The vertical axis of FIG. 3A is an acceleration Ax along the first axis. The vertical axis of FIG. 3B is an acceleration Ay along the second axis. The vertical axis of FIG. 3C is an acceleration Az along the third axis.

As shown in FIGS. 3A to 3C, accelerations that relate to the three axes are detected in the first cycle T1. As shown in FIG. 3A, a first component threshold value V1 that relates to a first component A1 (e.g., a positive value) along the first axis and a fourth component threshold value V4 that relates to a fourth component A4 (e.g., a negative value) along the first axis are established. For example, the movement of the hand 81 relating to the first axis is large when the first component A1 (e.g., a positive value) exceeds the first component threshold value V1. For example, the movement of the hand 81 relating to the first axis is large when the absolute value of the fourth component A4 (e.g., a negative value) exceeds the fourth component threshold value V4.

Similarly, as shown in FIG. 3B, a second component threshold value V2 that relates to a second component A2 (e.g., a negative value) along the second axis and a fifth component threshold value V5 that relates to a fifth component A5 (e.g., a negative value) along the second axis are established. As shown in FIG. 3C, a third component threshold value V3 that relates to a third component A3 (e.g., a negative value) along the third axis and a sixth component threshold value V6 that relates to a sixth component A6 (e.g., a negative value) along the third axis are established.

In the embodiment, the processor 12 can determine whether the person 80 is scratching based on at least one of such six components relating to the acceleration. For example, when at least one of such six components exceeds the threshold value, it is determined that the person 80 is scratching. Such determination operation is executed in a second cycle T2 (referring to FIGS. 3A to 3C).

The second cycle T2 is, for example, not less than 0.5 seconds and not more than 3 seconds. In one example, the second cycle T2 is not less than 10 times and not more than 50 times, e.g., 25 times the first cycle T1.

For example, the processor 12 is configured to perform the following determination operation based on the first signal S1. The second cycle T2 includes multiple first cycles T1. For example, the determination operation is executed for each second cycle T2. The determination operation includes detecting whether the person 80 is scratching based on multiple parameters.

In one example, the multiple parameters include the following first occurrence count and the following first consecutive count. The first occurrence count is the number of times that the absolute value of the detected value (e.g., the component of the acceleration relating to one of the three axes) exceeds the threshold value in one of the second cycles T2. The first consecutive count is the maximum value of the number of times that the absolute value of the detected value consecutively exceeds the threshold value in one of the second cycles T2. It was found that scratching behavior can be more accurately detected by detecting whether the person 80 is scratching based on such multiple parameters.

In one example, positive acceleration components (the first component A1, the second component A2, and the third component A3) may be used as the detected value. In such a case, in the example of FIG. 3A, the number of times (the first occurrence count) that the positive acceleration Ax exceeds the first component threshold value V1 in one of the second cycles T2 is 11. In the example of FIG. 3A, the maximum value (the first consecutive count) of the number of times that the absolute value of the detected value consecutively exceeds the threshold value in one of the second cycles T2 is 9. The processor 12 detects whether the person 80 is scratching based on such an occurrence count and such a consecutive count regarding one of the three axes. It is determined that the person 80 is scratching when the occurrence count and the consecutive count (or a function of these) regarding the positive acceleration Ax are greater than threshold values. It is determined that the person 80 is not scratching when the occurrence count and the consecutive count (or a function of these) regarding the positive acceleration Ax are not more than the threshold values.

It can be determined that the person 80 is scratching when the occurrence count and the consecutive count (or a function of these) regarding the positive acceleration Ay are greater than threshold values, even if the occurrence count and the consecutive count (or a function of these) regarding the positive acceleration Ax are not more than the threshold values.

It can be determined that the person 80 is scratching when the occurrence count and the consecutive count (or a function of these) regarding the positive acceleration Az are greater than threshold values, even if the occurrence count and the consecutive count (or a function of these) regarding the positive acceleration Ay and the positive acceleration Ax are not more than the threshold values.

For example, whether the person 80 is scratching may be comprehensively determined by performing such processing for the three axes. For example, the scratching may be determined using the result of a calculation (including the sum, etc.) of detected values relating to two or more of the three axes.

In the embodiment, the multiple parameters may further include the following first average count. The first average count is the average value of the absolute values of the detected value exceeding the threshold value in one of the second cycles T2. For example, in the example of FIG. 3A, the absolute value of the detected value (e.g., the positive acceleration Ax) exceeding the threshold value (e.g., the first component threshold value V1) in one of the second cycles T2 is averaged. In the example of FIG. 3A, eleven detected values (e.g., the positive accelerations Ax) exceed the threshold value (e.g., the first component threshold value V1). The average value of the eleven detected values (e.g., the positive accelerations Ax) corresponds to the first average count. The scratching can be more accurately detected by detecting whether the person 80 is scratching based on multiple parameters that include the first average count.

In the embodiment, the scratching behavior may be detected by considering positive and negative accelerations relating to the three axes.

For example, as described above, the detected value in the first signal S1 may include the first to sixth components A1 to A6 described above. The first component A1 is the component of one of positive or negative along the first axis of the acceleration. The second component A2 is the component of one of positive or negative along the second axis of the acceleration. The third component A3 is the component of one of positive or negative along the third axis of the acceleration. The fourth component A4 is the component of the other of positive or negative along the first axis of the acceleration. The fifth component A5 is the component of the other of positive or negative along the second axis of the acceleration. The sixth component A6 is the component of the other of positive or negative along the third axis of the acceleration. The processor 12 is configured to perform the determination operation which includes determining the person 80 is scratching when at least one of a first axis parameter based on the first and fourth components A1 and A4, a second axis parameter based on the second and fifth components A2 and A5, or a third axis parameter based on the third and sixth components A3 and A6 exceeds a threshold value.

For example, a first axis parameter P1 is represented by $$P1 = n1 \times N1 + c1 \times C1 + m1 \times M1 + n4 \times N4 + c4 \times C4 + m4 \times M4 \qquad (1)$$

"N1" is the number of times that the absolute value of the first component A1 exceeds the absolute value of the first component threshold value V1 relating to the first component A1 in one of the second cycles T2. "C1" is the maximum value of the number of times that the absolute value of the first component A1 consecutively exceeds the absolute value of the first component threshold value V1 in one of the second cycles T2. "M1" is the average value of the absolute values of the first component A1 exceeding the absolute value of the first component threshold value V1 in one of the second cycles T2. "n1" is a coefficient. "c1" is a coefficient. "m1" is a coefficient. These coefficients are, for example, positive. "N4" is the number of times that the absolute value of the fourth component A4 exceeds the absolute value of the fourth component threshold value V4 relating to the fourth component A4 in one of the second cycles T2. "C4" is the maximum value of the number of times that the absolute value of the fourth component A4 consecutively exceeds the absolute value of the fourth component threshold value V4 in one of the second cycles T2. "M4" is the average value of the absolute values of the fourth component A4 exceeding the absolute value of the fourth component threshold value V4 in one of the second cycles T2. "n4" is a coefficient. "c4" is a coefficient. "m4" is a coefficient. For example, "n1", "n4", "m1", and "m4" are one of positive or negative, and "c1" and "c4" are the other of positive or negative. For example, "n1", "n4", "m1", and "m4" are positive, and "c1" and "c4" are negative.

For example, a second axis parameter P2 is represented by $$P2 = n2 \times N2 + c2 \times C2 + m2 \times M2 + n5 \times N5 + c5 \times C5 + m5 \times M5 \quad (2)$$

"N2" is the number of times that the absolute value of the second component A2 exceeds the absolute value of the second component threshold value V2 relating to the second component A2 in one of the second cycles T2. "C2" is the maximum value of the number of times that the absolute value of the second component A2 consecutively exceeds the absolute value of the second component threshold value V2 in one of the second cycles T2. "M2" is the average value of the absolute values of the second component A2 exceeding the absolute value of the second component threshold value V2 in one of the second cycles T2. "n2" is a coefficient. "c2" is a coefficient. "m2" is a coefficient. "N5" is the number of times that the absolute value of the fifth component A5 exceeds the absolute value of the fifth component threshold value V5 relating to the fifth component A5 in one of the second cycles T2. "C5" is the maximum value of the number of times that the absolute value of the fifth component A5 consecutively exceeds the absolute value of the fifth component threshold value V5 in one of the second cycles T2. "M5" is the average value of the absolute values of the fifth component A5 exceeding the absolute value of the fifth component threshold value V5 in one of the second cycles T2. "n5" is a coefficient. "c5" is a coefficient. "m5" is a coefficient. For example, "n2", "n5", "m2", and "m5" are one of positive or negative, and "c2" and "c5" are the other of positive or negative. For example, "n2", "n5", "m2", and "m5" are positive, and "c2" and "c5" are negative.

For example, a third axis parameter P3 is represented by $$P3 = n3 \times N3 + c3 \times C3 + m3 \times M3 + n6 \times N6 + c6 \times C6 + m6 \times M6 \quad (3)$$

"N3" is the number of times that the absolute value of the third component A3 exceeds the absolute value of the third component threshold value V3 relating to the third component A3 in one of the second cycles T2. "C3" is the maximum value of the number of times that the absolute value of the third component A3 consecutively exceeds the absolute value of the third component threshold value V3 in one of the second cycles T2. "M3" is the average value of the absolute values of the third component A3 exceeding the absolute value of the third component threshold value V3 in one of the second cycles T2. "n3" is a coefficient. "c3" is a coefficient. "m3" is a coefficient. "N6" is the number of times that the absolute value of the sixth component A6 exceeds the absolute value of the sixth component threshold value V6 relating to the sixth component A6 in one of the second cycles T2. "C6" is the maximum value of the number of times that the absolute value of the sixth component A6 consecutively exceeds the absolute value of the sixth component threshold value V6 in one of the second cycles T2. "M6" is the average value of the absolute values of the sixth component A6 exceeding the absolute value of the sixth component threshold value V6 in one of the second cycles T2. "n6" is a coefficient. "c6" is a coefficient. "m6" is a coefficient. For example, "n3", "n6", "m3", and "m6" are one of positive or negative, and "c3" and "c6" are the other of positive or negative. For example, "n3", "n6", "m3", and "m6" are positive, and "c3" and "c6" are negative.

As described below, it was found that the detection result using the first to third axis parameters P1 to P3 such as those described above had a good match to the actual observation result indicating whether the person 80 is scratching. For example, "N1" corresponds to the number of times that the absolute value of the acceleration exceeds the absolute value of the threshold value. The scratching behavior of the person 80 corresponds to a back and forth motion (a repeated movement) of the hand. Accordingly, it is considered that "N1" becomes relatively large when the person 80 is scratching. On the other hand, "C1" is the number of times that the absolute value of the acceleration consecutively exceeds the absolute value of the threshold value. The movement of the person 80 seems not to correspond to a back and forth motion of the hand when the number of times (i.e., duration of the acceleration) that the absolute value of the acceleration consecutively exceeds the absolute value of the threshold value. Accordingly, it is considered that scratching behavior can be more accurately evaluated by removing the movement of "C1", which does not correspond to scratching behavior, from the movement corresponding to "N1", which indicates the simple number of times. For example, by setting "n1" to be positive and "c1" to be negative, the effects of "C1", which does not correspond to scratching, can be effectively removed.

For example, by using "N1" and "C1", by setting the coefficient "n1" to one of positive or negative, and by setting "c1" to the other of positive or negative, the effects of "C1", which does not correspond to scratching behavior, can be removed more effectively than the result of the evaluation using only "N1".

The description of the coefficients described above is applicable also to the other axes. For example, coefficients n1, n2, n3, n4, n5, and n6 are one of positive or negative, and coefficients c1, c2, c3, c4, c5, and c6 are the other of positive or negative. The effects of the acceleration (the movement) that does not correspond to scratching behavior can be effectively removed thereby.

In the embodiment, it is favorable for the absolute value of "n1" to be not less than 1/5 and not more than 5 times the absolute value of "c1". It is favorable for the absolute value of "n2" to be not less than 1/5 and not more than 5 times the absolute value of "c2". It is favorable for the absolute value of "n3" to be not less than 1/5 and not more than 5 times the absolute value of "c3". It is favorable for the absolute value of "n4" to be not less than 1/5 and not more than 5 times the absolute value of "c4". It is favorable for the absolute value of "n5" to be not less than 1/5 and not more than 5 times the absolute value of "c5". It is favorable for the absolute value of "n6" to be not less than 1/5 and not more than 5 times the absolute value of "c6". For example, "N1" to "N6" are values corresponding to the occurrence count (the number of times in the second cycle T2), and "C1" to "C6" correspond to the consecutive occurrence count. Accordingly, the units of the values of "N1" to "N6" are the same as the units of the values of "C1" to "C6". Accordingly, because the absolute values of the coefficients n1, n2, n3, n4, n5, and n6 are relatively near the absolute values of the coefficients c1, c2, c3, c4, c5, and c6, the effects of the acceleration (the movement) that does not correspond to scratching can be effectively removed.

In the embodiment, the polarity (positive of negative) of coefficients m1 to m6 is the same as the polarity (positive of negative) of the coefficients n1 to n6. For example, "M1" corresponds to the magnitude of the acceleration. A large "M1" corresponds to a movement of the person 80 being scratching. Because the polarity (positive of negative) of the coefficients m1 to m6 is the same as the polarity (positive of negative) of the coefficients n1 to n6, the scratching behavior can be more accurately determined (and detected).

The first to sixth components A1 to A6 can be defined by using the acceleration G due to gravity, for example. The acceleration G due to gravity is, for example, 9.806 m/s². When the first to third components A1 to A3 are positive, the first to third component threshold values V1 to V3 are, for example, 0.035 G. When the fourth to sixth components A4 to A6 are negative, the fourth to sixth component threshold values V4 to V6 are, for example, −0.035 G.

By such first to third axis parameters P1 to P3, the scratching behavior of the person 80 can be detected with high accuracy.

Figure 4:
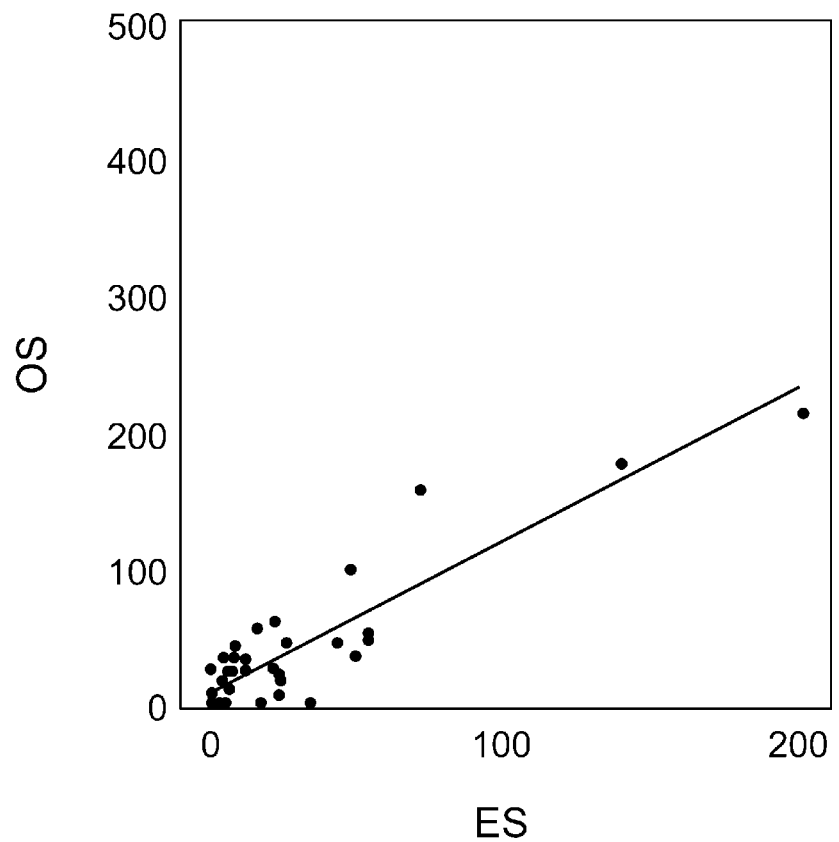
FIG. 4 is a graph illustrating a characteristic obtained by the scratching detection system according to the first embodiment.

FIG. 4 is a graph illustrating a characteristic obtained by the scratching detection system according to the first embodiment.

FIG. 4 illustrates the result of evaluating the scratching behavior of the person 80 in one evaluation period. The horizontal axis of FIG. 4 corresponds to the result of the processor 12 detecting the scratching behavior based on the first to third axis parameters P1 to P3 described above. The horizontal axis of FIG. 4 is an estimated scratching time ES in which it is determined that the person 80 is scratching. The vertical axis corresponds to the result of detecting the scratching behavior from the result of imaging the person 80. The vertical axis is an observed scratching time OS in which it is determined that the person 80 is scratching from the imaging result. In the example of FIG. 4, the first to third parameters P1 to P3 are represented by Formulas (1) to (3) described above.

As shown in FIG. 4, the estimated scratching time ES has a good match with the observed scratching time OS. Spearman's correlation coefficient of the two is 0.722.

In the embodiment, the first axis parameter P1 may be represented by $$P1 = n1 \times N1 + c1 \times C1 + n4 \times N4 + c4 \times C4 \quad (4)$$

The second axis parameter P2 may be represented by $$P2 = n2 \times N2 + c2 \times C2 + n5 \times N5 + c5 \times C5 \quad (5)$$

The third axis parameter P3 may be represented by $$P3 = n3 \times N3 + c3 \times C3 + n6 \times N6 + c6 \times C6 \quad (6)$$

The scratching can be detected with relatively high accuracy even when the determination operation is executed based on the first to third axis parameters P1 to P3. The motion seems not to correspond to a back and forth motion when the number of times that the detected value of the acceleration consecutively exceeds the threshold value is large. The scratching behavior can be detected with relatively high accuracy by employing a parameter that excludes the number of times that the acceleration consecutively exceeds the threshold value from the number of times that the detected value of the acceleration exceeds the threshold value.

In the embodiment, the scratching behavior may be detected based on the acceleration that is one of positive or negative. For example, the detected value includes the first to third components A1 to A3 described above. The determination operation of the processor 12 may include, for example, determining that the person 80 is scratching when at least one of the first axis parameter P1 based on the first component A1, the second axis parameter P2 based on the second component A2, or the third axis parameter P3 based on the third component A3 exceeds a threshold value.

For example, the first axis parameter P1 may be represented by $$P1 = n1 \times N1 + c1 \times C1 \quad (7)$$

As described above, "N1" is the number of times that the absolute value of the first component A1 exceeds the absolute value of the first component threshold value V1 in one of the second cycles T2. "C1" is the maximum value of the number of times that the absolute value of the first component A1 consecutively exceeds the absolute value of the first component threshold value V1 in one of the second cycles T2.

The second axis parameter P2 may be represented by $$P2 = n2 \times N2 + c2 \times C2 \quad (8)$$

As described above, "N2" is the number of times that the absolute value of the second component A2 exceeds the absolute value of the second component threshold value V2 in one of the second cycles T2. "C2" is the maximum value of the number of times that the absolute value of the second component A2 consecutively exceeds the absolute value of the second component threshold value V2 in one of the second cycles T2.

The third axis parameter P3 may be represented by $$P3 = n3 \times N3 + c3 \times C3 \quad (9)$$

As described above, "N3" is the number of times that the absolute value of the third component A3 exceeds the absolute value of the third component threshold value V3 in one of the second cycles T2. "C3" is the maximum value of the number of times that the absolute value of the third component A3 consecutively exceeds the absolute value of the third component threshold value V3 in one of the second cycles T2. The scratching behavior can be detected with relatively high accuracy even when the determination operation is performed based on such first to third axis parameters P1 to P3. As described above, it is considered that the scratching behavior corresponds to a repeated movement of the hand. Accordingly, it is considered that scratching behavior can be detected with relatively high accuracy by evaluating using a parameter relating to the movement toward one of positive or negative.

Figure 5:
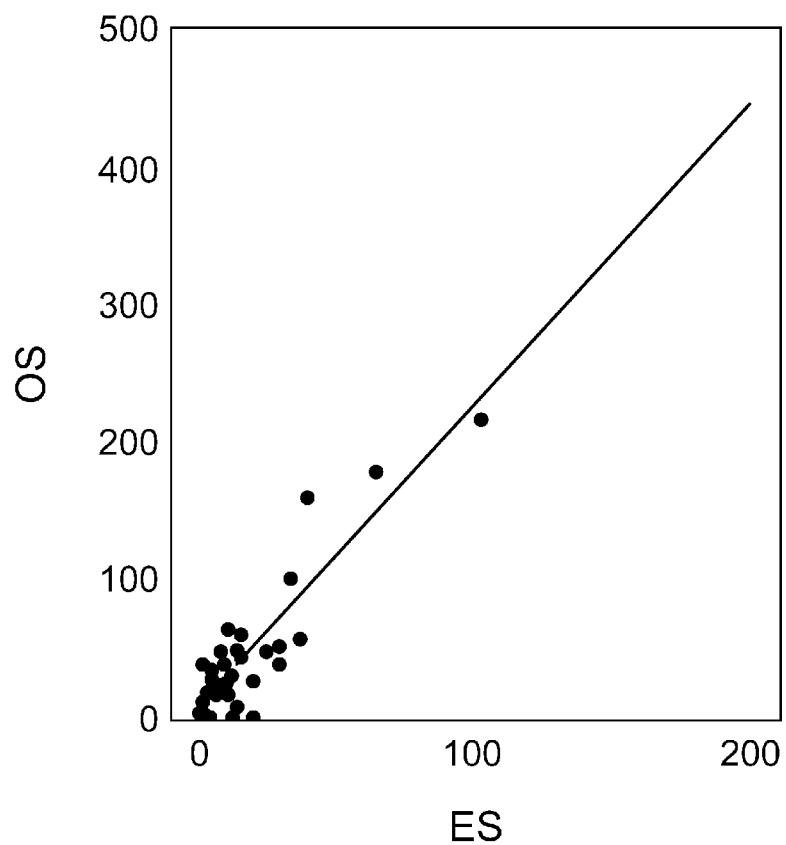
FIG. 5 is a graph illustrating a characteristic obtained by the scratching detection system according to the first embodiment.

FIG. 5 is a graph illustrating a characteristic obtained by the scratching detection system according to the first embodiment.

In the example of FIG. 5, the first to third parameters P1 to P3 are represented by Formulas (7) to (9) described above. The horizontal axis of FIG. 5 corresponds to the result of the processor 12 detecting the scratching of the person 80 based on such first to third axis parameters P1 to P3. The horizontal axis of FIG. 5 is the estimated scratching time ES in which it is determined that the person 80 is scratching. The vertical axis is the observed scratching time OS in which it is determined that the person 80 is scratching from the imaging result. As shown in FIG. 5, even when Formulas (7) to (9) are used, the estimated scratching time ES has a good match with the observed scratching time OS. Spearman's correlation coefficient of the two is 0.730. Comparing the result of FIG. 4 and the result of FIG. 5, the slopes of the actual measured value (the vertical axis) with respect to the predicted value (the horizontal axis) are different from each other. For this aspect, it is considered that scratching can be evaluated with higher accuracy by employing Formulas (1) to (3).

In the embodiment, the first axis parameter P1 may be represented by $$P1 = n1 \times N1 + c1 \times C1 + m1 \times M1 \quad (10)$$

The second axis parameter P2 may be represented by $$P2 = n2 \times N2 + c2 \times C2 + m2 \times M2 \quad (11)$$

The third axis parameter P3 may be represented by $$P3 = n3 \times N3 + c3 \times C3 + m3 \times M3 \quad (12)$$

Figure 6:
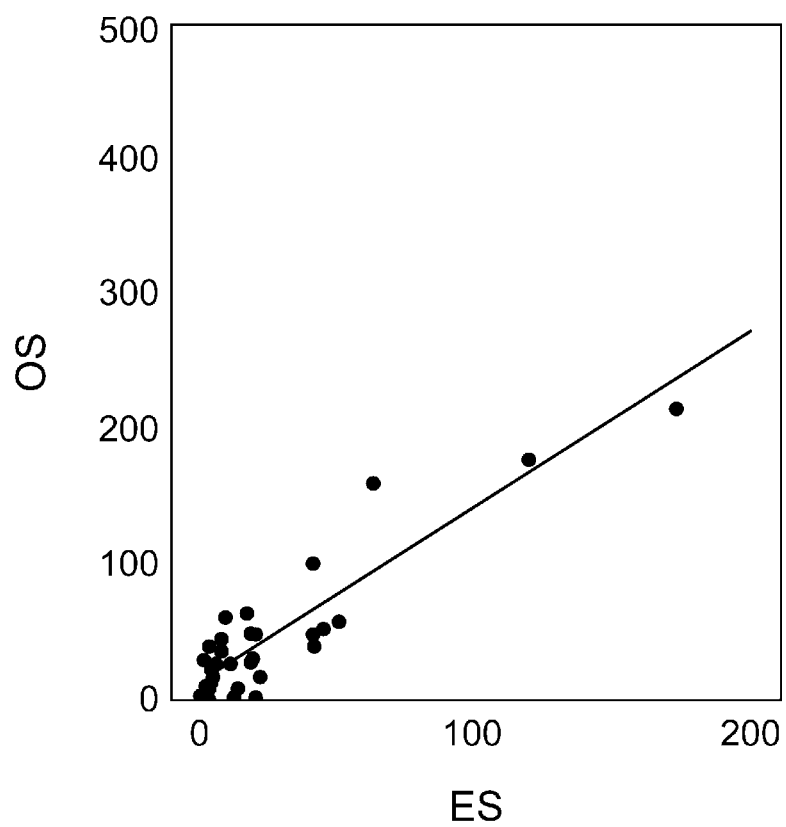
FIG. 6 is a graph illustrating a characteristic obtained by the scratching detection system according to the first embodiment.

FIG. 6 is a graph illustrating a characteristic obtained by the scratching detection system according to the first embodiment.

In the example of FIG. 6, the first to third parameters P1 to P3 are represented by Formulas (10) to (12) described above. The horizontal axis of FIG. 6 corresponds to the result of the processor 12 detecting the scratching of the person 80 based on such first to third axis parameters P1 to P3. The horizontal axis of FIG. 6 is the estimated scratching time ES in which it is determined that the person 80 is scratching. The vertical axis is the observed scratching time OS in which it is determined that the person 80 is scratching from the imaging result. As shown in FIG. 6, even when Formulas (10) to (12) are used, the estimated scratching time ES has a good match with the observed scratching time OS. Spearman's correlation coefficient of the two is 0.737. Comparing the result of FIG. 4 and the result of FIG. 6, the slopes of the actual measured value (the vertical axis) with respect to the predicted value (the horizontal axis) are slightly different. For this aspect, it is considered that scratching can be evaluated with higher accuracy by employing Formulas (1) to (3).

In the embodiment, for example, when the first axis is along the direction of the acceleration due to the movement of the hand 81 associated with the scratching behavior, there are cases where the scratching behavior can be accurately evaluated by an evaluation relating to the first axis. In such a case, the evaluations that relate to the second and third axes may not be performed. For example, the evaluation may be performed using a parameter relating to at least one of the first to third axes. For example, the scratching behavior may be determined using at least one of the first to third axis parameters P1 to P3.

In the embodiment described above, the processor 12 detects whether the person 80 is scratching from the comparison result between the calculation result of the first to third axis parameters and their corresponding threshold values (e.g., thresholds). As described above, the first to third axis parameters P1-P3 can be defined by one of equation sets of a first set (1)-(3), a second set (4)-(6), a third set (7)-(9), and a fourth set (10)-(12), for example. In the embodiment, one of the axis parameters can be defined by one of the equation sets, and other one of the axis parameters can be defined by different one of the equation sets. For example, the determination operation may include performing such multiple processing (e.g., the first processing, the second processing, etc.). For example, the determination operation may include a first processing based on the first equation set, and a second processing based on the second equation set. Further, the determination operation may include a first processing that relates to the first axis parameter and a second processing that relates to the second axis parameter. Then, as described above, at least one of the first processing or the second processing may include detecting (determining) the scratching behavior by comparing between the detected value relating to at least one of the first to third axes and corresponding threshold value.

The parameters (including the coefficients), etc., that are described above may be preset. In the scratching detection system, multiple modes may be provided, and different parameters (including coefficients) may be employed in the multiple modes. The parameters (including the coefficients) may be modifiable to match the state of the person 80. The coefficients of the parameters may be corrected by machine learning, etc.

An example of the determination operation (i.e., the first operation) performed by the processor 12 will now be described.

Figure 7:
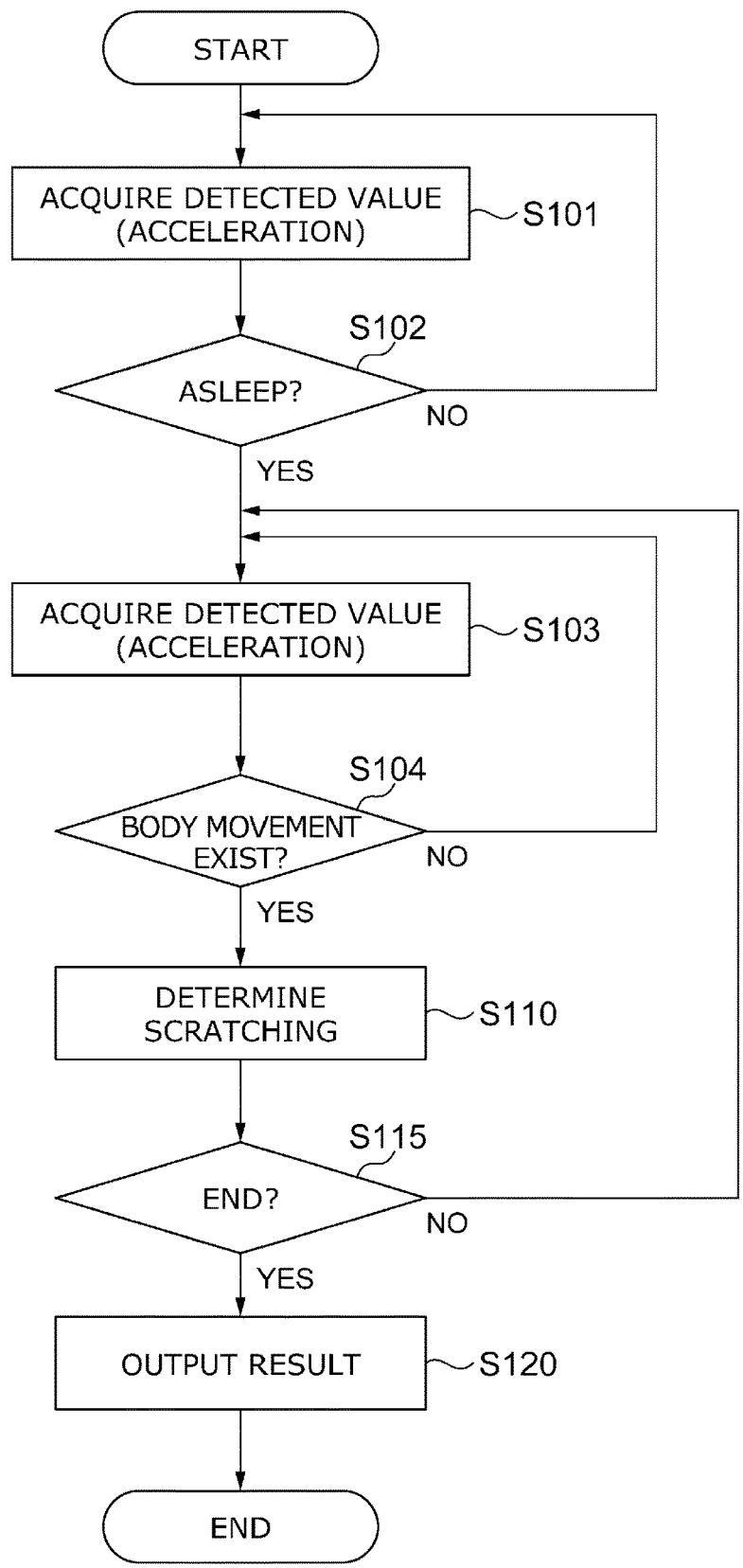
FIG. 7 is a flowchart illustrating the operation of the scratching detection system according to the embodiment.

FIG. 7 is a flowchart illustrating the operation of the scratching detection system according to the embodiment.

FIG. 7 illustrates the operation of the processor 12 of the measuring device 10. An example of detecting the scratching behavior while sleeping will now be described.

As shown in FIG. 7, the processor 12 acquires the first signal S1 including the detected value (the acceleration) from the sensor 11 (step S101). In one example, the processor 12 acquires the detected value in the first cycle T1.

In the example, the processor 12 determines whether or not the person 80 is asleep based on the detected value (step S102). When determined to be asleep, the flow proceeds to the next step S103. When determined not to be asleep, step S101 and step S102 are repeated. In step S102, for example, sleeping is determined to be when a state in which the detected value (the acceleration) is less than a certain threshold value continues for not less than a predefined time.

In step S103, the processor 12 acquires the first signal S1 including the detected value (the acceleration) from the sensor 11. For example, the processor 12 acquires the detected value in the first cycle T1.

The processor 12 determines the body movement of the person 80 (the movement of the hand 81) based on the detected value (the acceleration) acquired in step S103 (and step S104). At this time, for example, the processor 12 determines whether there is relatively large body movement or not based on the following movement parameters.

For example, the detected value includes a first acceleration component B1 along the first axis of the acceleration, a second acceleration component B2 along the second axis of the acceleration, and a third acceleration component B3 along the third axis of the acceleration. The second axis crosses the first axis. The third axis crosses a plane including the first and second axes. The processor 12 determines that the hand 81 has moved when the following movement parameter exceeds the threshold values relating to the movement parameter. The movement parameter is the root mean square of the first acceleration component B1, the second acceleration component B2, and the third acceleration component B3.

For example, a movement parameter $P_m$ is represented by $Pm = ((B1)^2 + (B2)^2 + (B3)^2)^{1/2}$ using the first acceleration component B1, the second acceleration component B2, and the third acceleration component B3. The processor 12 determines that there is body movement (a movement of the hand 81) when such a movement parameter $P_m$ exceeds the threshold value. When the first acceleration component B1, the second acceleration component B2, and the third acceleration component B3 are the acceleration due to gravity, in one example, the threshold value that relates to the parameter $P_m$ is 0.03 G or more, for example. For example, the threshold value that relates to the parameter $P_m$ may be 0.1 G or less. Whether there is relatively large body movement of the hand 81 is determined by comparing such a threshold value and the movement parameter $P_m$.

When the processor 12 determines that there is no body movement or relatively small body movement (movement of the hand 81) in step S104, the flow returns to step S103. When the processor 12 determines that there is body movement (movement of the hand 81) in step S104, the flow proceeds to the following step S110.

In step S110, the processor 12 performs the determination operation including the first processing described above and performs the determination of scratching behavior. For example, the processor 12 determines whether the person 80 is scratching based on at least one of the multiple parameters (the first to third axis parameters P1 to P3, etc.) described above. The determination whether the person 80 is scratching is repeatedly performed in the second cycle T2.

In the example, it is determined whether or not the sleeping has ended (step S115). When the sleeping has not ended, the flow returns to step S103, and the processing described above is repeated.

In the example, when the sleeping has ended and the measurement has ended, for example, the processor 12 outputs the scratching result (the detection result) to an external communication device or the like (step S120). For example, the detection result is output to the output device 20. For example, the detection result may be performed at any step between step S103 to step S115.

For example, in the determination operation, the first processing includes outputting the detection result of the scratching behavior for each second cycle T2. For example, the first processing may include outputting the detection result of the scratching behavior in the second cycle T2.

As described above, the processor 12 may be configured to perform the determination operation when the hand 81 is determined to have moved based on the first signal S1 (step S104). The amount of processing can be reduced by performing the first processing that determines the person 80 is scratching when the hand 81 is determined to have moved. For example, the power consumption can be reduced.

An example of the operation of the output device 20 will now be described.

Figure 8:
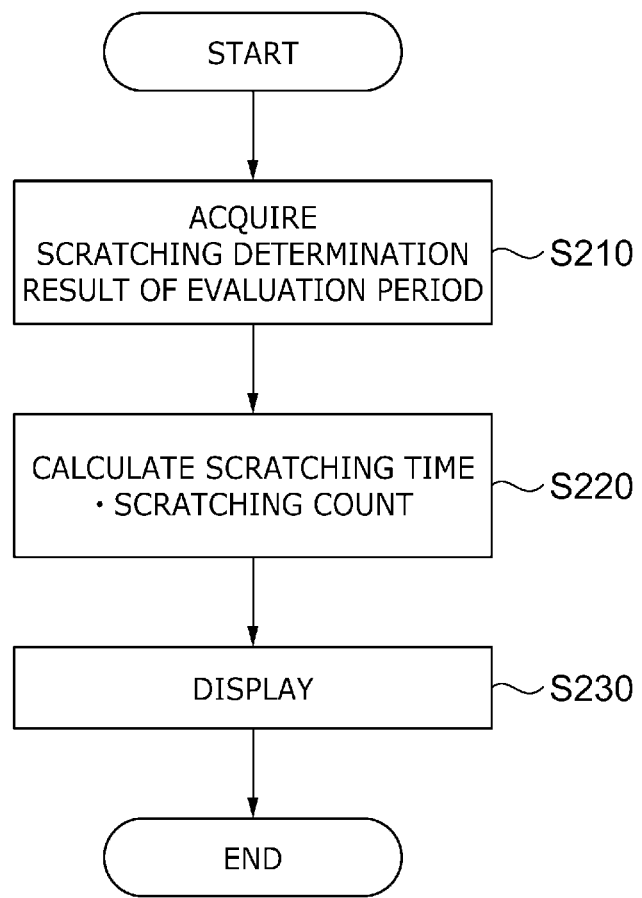
FIG. 8 is a flowchart illustrating the operation of the scratching detection system according to the embodiment.

FIG. 8 is a flowchart illustrating the operation of the scratching detection system according to the embodiment.

As shown in FIG. 8, the output device 20 acquires the detection result relating to whether the person 80 is scratching from the measuring device 10 (step S210). For example, the processor 22 of the output device 20 acquires the detection result relating to whether the person 80 is scratching in an evaluation period (e.g., one sleep period, etc.) designated via the communicator 13 and the communicator 23.

The processor 22 of the output device 20 performs a calculation for the scratching time, the scratching count, etc. (step S220). For example, based on the detection result relating to whether the person 80 is scratching, the processor 22 is configured to generate information relating to at least one of the scratching count, the scratching time, or the relative scratching time from the calculation. The scratching count is the number of the second cycles T2 in which scratching behavior is determined in the evaluation period that includes the multiple second cycles T2. The scratching time is the sum of the consecutive second cycles T2 in the evaluation period in which scratching behavior is determined. The relative scratching time is the ratio of the scratching time to the evaluation period (the length thereof).

The display 21 of the output device 20 displays such information (step S230). For example, the display 21 is configured to display the information relating to at least one of the scratching count, the scratching time, or the relative scratching time.

The display 21 may be configured to display at least one of whether the person 80 is scratching, the first occurrence count described above, or the first consecutive count described above acquired from the measuring device 10.

In the embodiment, scratching behavior that is detected with high accuracy can be displayed.

At least a portion of the processing performed by the processor 22 of the output device 20 may be performed by the server 30 (referring to FIG. 1). The output device 20 may acquire the result of the processing performed by the server 30, and the display 21 may display the result.

Figure 9:
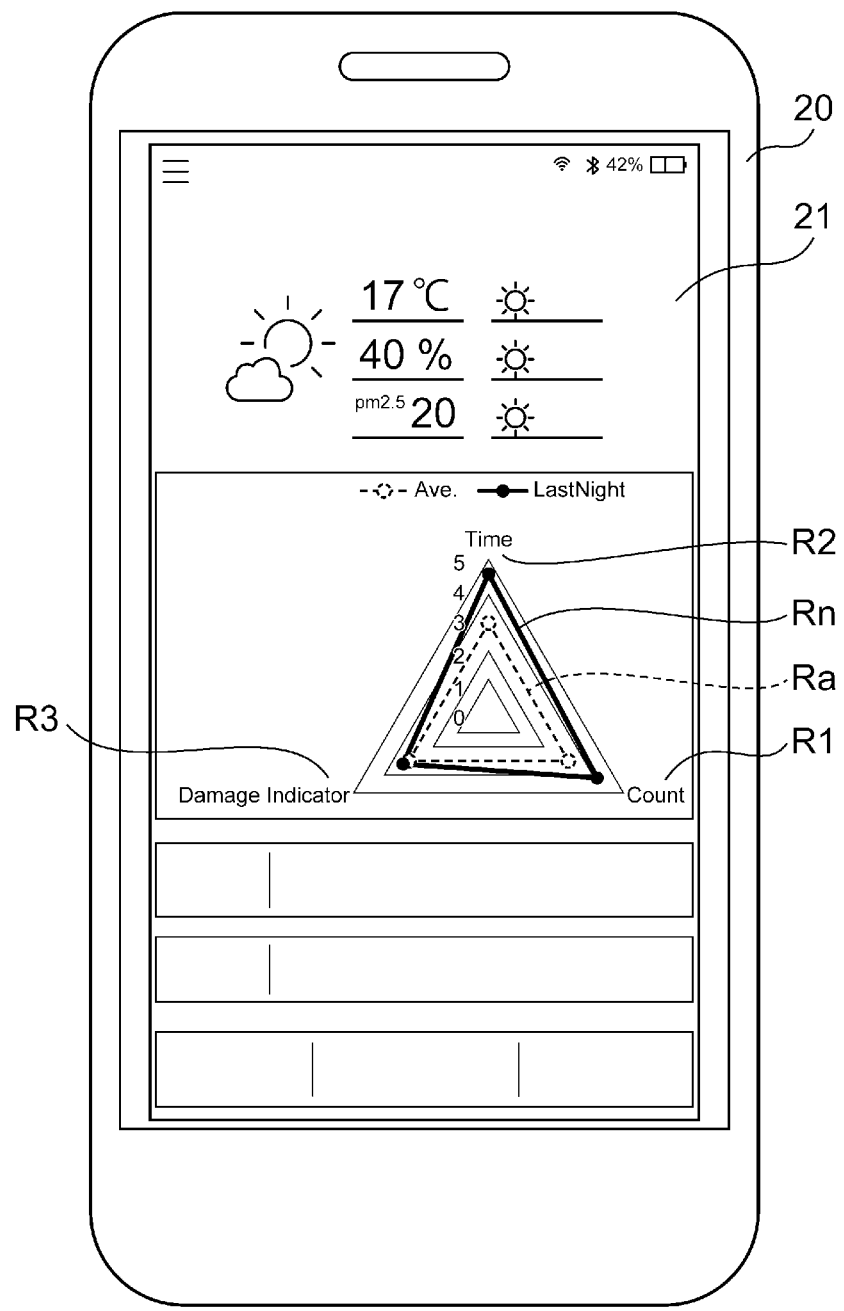
FIG. 9 is a schematic view illustrating an output device of the scratching detection system according to the embodiment.

FIG. 9 is a schematic view illustrating an output device of the scratching detection system according to the embodiment. As shown in FIG. 9, the output device 20 includes the display 21. In the example, for example, the display 21 displays a scratching count R1 and a scratching time R2 by using figures. The display 21 may be configured to display a scratching intensity R3. In the example, the scratching intensity R3 corresponds to the sum in the second cycle T2 of the sums of "M1" to "M6" at times at which scratching behavior is determined. In the example, average data Ra of a prescribed period is displayed in addition to newest data Rn.

Figure 10:
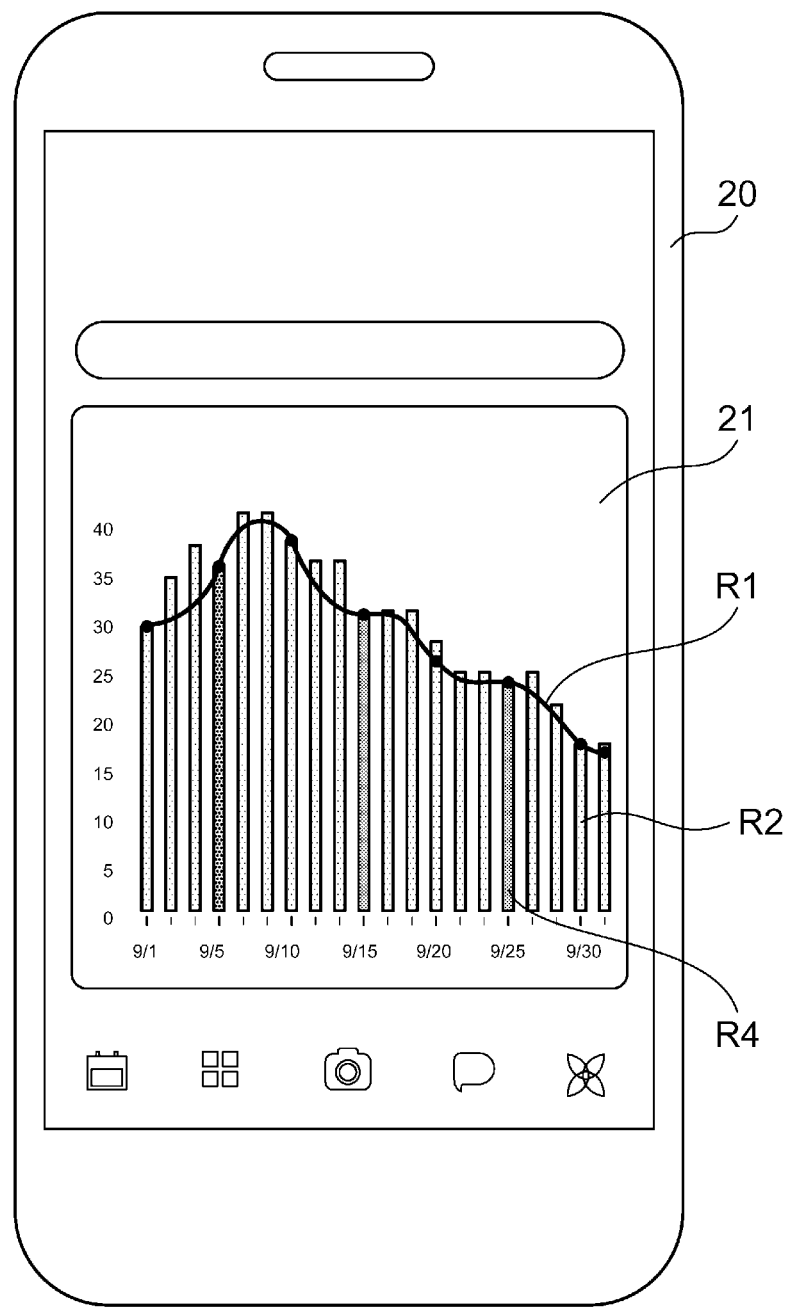
FIG. 10 is a schematic view illustrating an output device of the scratching detection system according to the embodiment.

FIG. 10 is a schematic view illustrating an output device of the scratching detection system according to the embodiment. As shown in FIG. 10, the display 21 of the output device 20 may be configured to display the change by day of the scratching count R1, the scratching time R2, etc., in a graph, etc. In the example, the scratching count R1 is displayed as a line. The scratching time R2 is displayed in a bar graph. In the example, the display 21 is configured to display information relating to a skin damage index of the person 80 by using shading (colors, etc.) of the bar graph.

For example, there is a reference example that directly measures the scratching count for a measurement time. Conversely, in the embodiment, whether the person 80 is scratching is determined for each second cycle T2. In the embodiment, the calculation amount can be reduced thereby. For example, the measuring device 10 can be downsized. For example, the power consumption of the measuring device 10 can be reduced. In the embodiment, for example, the scratching can be determined in substantially real time for each second cycle T2.

For example, a mountable measuring device 10 of the hand 81 of the person 80 is used. In the measuring device 10, whether the person 80 is scratching is determined for each second cycle T2 (e.g., 1 second, etc.). The result of the determination may be stored in the memory 14, etc. For example, the result can be supplied to the output device 20 by wireless communication or wired communication. The output device 20 is configured to display the information relating to whether the person 80 is scratching. The output device 20 may be configured to supply the information relating to whether the person 80 is scratching that is acquired to the server 30, etc., via the cloud (e.g., the network 35) by any wireless communication or wired communication. The output device 20 may be configured to receive analysis data from the cloud and may be configured to display the analysis data in the display 21 of the output device 20.

For example, the server 30 is configured to store and manage the information (the data) acquired from the output device 20. The server 30 may be configured to supply the analysis result to the output device 20.

For example, the processor 12 of the measuring device 10 determines whether the person 80 is scratching by calculating a feature for each second cycle T2. The processor 22 or the server 30 acquires the result and calculates the scratching time, the scratching count, etc., for the evaluation period. The output device 20 displays this data and notifies the person 80 or a staff member (a health care professional, etc.) of the person 80.

Figure 11:
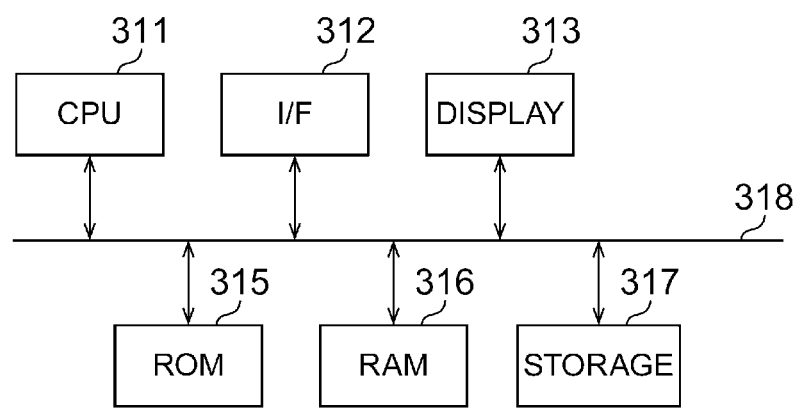
FIG. 11 is a schematic view illustrating a processing device according to the embodiment.

FIG. 11 is a schematic view illustrating a processing device according to the embodiment.

FIG. 11 shows an example of a processing device of the processor 12, the processor 22, the server 30, etc. FIG. 11 is a functional block diagram. As shown in FIG. 11, the processing device includes, for example, a CPU (Central Processing Unit) 311, an I/F 312, a display 313, ROM (Read Only Memory) 315, RAM (Random Access Memory) 316, a memory device 317, etc. The various operations described above are performed by, for example, a CPU. For example, the multiple components that are included in the processing device can communicate using a communication path 318, etc. The communication may be wired or wireless.

According to the embodiments, a scratching detection system can be provided in which scratching behavior can be more accurately detected.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in scratching detection systems such as measuring devices, sensors, processors, output devices, displays, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all scratching detection systems practicable by an appropriate design modification by one skilled in the art based on the scratching detection systems described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

REFERENCE NUMERAL LIST

10 measuring device
11 sensor
12 processor
13 communicator
14 memory
15 power supply
16 glove-shaped member
17 housing
18 adhesive member
19 power input terminal
19p protrusion
20 output device
21 display
22 processor
23 communicator
24 memory
25 power supply
30 server
35 network
80 person
81 hand
82 back
110 scratching detection system
313 display
315 ROM
316 RAM
317 memory device
318 communication path
A1 to A6 first to sixth components
Ax, Ay, Az accelerations
B1 to B3 first to third acceleration components
ES estimated scratching time
OS observed scratching time
R1 scratching count
R2 scratching time
R3 scratching intensity
Ra average data
Rn newest data
S1 first signal
T1 first cycle
T2 second cycle
V1 to V6 first to sixth component threshold values
tm time.

The invention claimed is:

1. A scratching detection system comprising:
a wearable sensor configured to be mounted in a fixed position on a hand of a person via one or more of: (1) a glove, or (2) an adhesive patch;
wherein the sensor is configured to detect an acceleration corresponding to a movement of the hand of the person;
wherein the sensor is configured to output a first signal including a detected value corresponding to the acceleration in a first cycle;
and a processor configured to
acquire the first signal and to detect a scratching behavior of the person in a second cycle based on a plurality of parameters,
the second cycle including a plurality of the first cycles,
the plurality of parameters including a first occurrence count and a first consecutive count,
the first occurrence count being a number of times that an absolute value of the detected value exceeds a threshold value in the second cycle,
the first consecutive count being a maximum value of a number of times that the absolute value of the detected value consecutively exceeds the threshold value in the second cycle;
and output a result of the detection to an output device, the output device including a display,
the display being configured to display a graphic chart depicting the result, the chart including at least one of the existence or absence of the scratching behavior, the first occurrence count, or the first consecutive count, where the existence or absence is displayed as a graphic trend on the chart.

2. The scratching detection system according to claim 1, wherein the plurality of parameters further includes a first average count,
and the first average count is an average value of the absolute values of the detected value exceeding the threshold value in the second cycle.

3. The scratching detection system according to claim 1, wherein the detected value includes a first component,
a second component,
and a third component,
the first component being one of positive or negative along a first axis of the acceleration,
the second component being one of positive or negative along a second axis of the acceleration,
the third component being one of positive or negative along a third axis of the acceleration,
the second axis crossing the first axis,
the third axis crossing a plane including the first and second axes,
the processor is configured to determine that the scratching behavior exists when at least one of a first axis parameter based on the first component,
a second axis parameter based on the second component,
or a third axis parameter based on the third component exceeds a determined value.

4. The scratching detection system according to claim 3, wherein the first axis parameter P1 is expressed by $P1 = n1 \times N1 + c1 \times C1$,
N1 is a number of times that an absolute value of the first component exceeds an absolute value of a first component threshold value relating to the first component in the second cycle,
C1 is a maximum value of a number of times that the absolute value of the first component consecutively exceeds the absolute value of the first component threshold value in the second cycle,
the second axis parameter P2 is expressed by $P2 = n2 \times N2 + c2 \times C2$,
N2 is a number of times that an absolute value of the second component exceeds an absolute value of a second component threshold value relating to the second component in the second cycle,
C2 is a maximum value of a number of times that the absolute value of the second component consecutively exceeds the absolute value of the second component threshold value in the second cycle,
the third axis parameter P3 is expressed by $P3 = n3 \times N3 + c3 \times C3$,
N3 is a number of times that an absolute value of the third component exceeds an absolute value of a third component threshold value relating to the third component in the second cycle,
C3 is a maximum value of a number of times that the absolute value of the third component consecutively exceeds the absolute value of the third component threshold value in the second cycle,
coefficients n1, n2, and n3 are one of positive or negative,
and coefficients c1, c2, and c3 are the other of positive or negative.

5. The scratching detection system according to claim 3, wherein the first axis parameter P1 is expressed by $P1 = n1 \times N1 + c1 \times C1 + m1 \times M1$,
N1 is a number of times that an absolute value of the first component exceeds an absolute value of a first component threshold value relating to the first component in the second cycle,
C1 is a maximum value of a number of times that the absolute value of the first component consecutively exceeds the absolute value of the first component threshold value in the second cycle,
M1 is an average value of the absolute values of the first component exceeding the absolute value of the first component threshold value in the second cycle,
the second axis parameter P2 is expressed by $P2 = n2 \times N2 + c2 \times C2 + m2 \times M2$,
N2 is a number of times that an absolute value of the second component exceeds an absolute value of a second component threshold value relating to the second component in the second cycle,
C2 is a maximum value of a number of times that the absolute value of the second component consecutively exceeds the absolute value of the second component threshold value in the second cycle,
M2 is an average value of the absolute values of the second component exceeding the absolute value of the second component threshold value in the second cycle,
the third axis parameter P3 is expressed by $P3 = n3 \times N3 + c3 \times C3 + m3 \times M3$,
N3 is a number of times that an absolute value of the third component exceeds an absolute value of a third component threshold value relating to the third component in the second cycle,
C3 is a maximum value of a number of times that the absolute value of the third component consecutively exceeds the absolute value of the third component threshold value in the second cycle,
M3 is an average value of the absolute values of the third component exceeding the absolute value of the third component threshold value in the second cycle,
coefficients n1, n2, n3, m1, m2, and m3 are one of positive or negative,
and coefficients c1, c2, and c3 are the other of positive or negative.

6. The scratching detection system according to claim 1, wherein the detected value includes a first component, a second component, a third component, a fourth component, a fifth component, and a sixth component,
the first component being one of positive or negative along a first axis of the acceleration,
the second component being one of positive or negative along a second axis of the acceleration,
the third component being one of positive or negative along a third axis of the acceleration,
the fourth component being the other of positive or negative along the first axis of the acceleration,
the fifth component being the other of positive or negative along the second axis of the acceleration,
the sixth component being the other of positive or negative along the third axis of the acceleration,
the second axis crosses the first axis,
the third axis crosses a plane including the first and second axes,
the processor is configured to determine that the scratching behavior exists when at least one of a first axis parameter based on the first and fourth components,
a second axis parameter based on the second and fifth components,
or a third axis parameter based on the third and sixth components exceeds an established value.

7. The scratching detection system according to claim 6, wherein the first axis parameter P1 is expressed by
P1=n1×N1+c1×C1+n4×N4+c4×C4,
N1 is a number of times that an absolute value of the first component exceeds an absolute value of a first component threshold value relating to the first component in the second cycle,
C1 is a maximum value of a number of times that the absolute value of the first component consecutively exceeds the absolute value of the first component threshold value in the second cycle,
N4 is a number of times that an absolute value of the fourth component exceeds an absolute value of a fourth component threshold value relating to the fourth component in the second cycle,
C4 is a maximum value of a number of times that the absolute value of the fourth component consecutively exceeds the absolute value of the fourth component threshold value in the second cycle,
the second axis parameter P2 is expressed by P2=n2×N2+c2×C2+n5×N5+c5×C5,
N2 is a number of times that an absolute value of the second component exceeds an absolute value of a second component threshold value relating to the second component in the second cycle,
C2 is a maximum value of a number of times that the absolute value of the second component consecutively exceeds the absolute value of the second component threshold value in the second cycle,
N5 is a number of times that an absolute value of the fifth component exceeds an absolute value of a fifth component threshold value relating to the fifth component in the second cycle,
C5 is a maximum value of a number of times that the absolute value of the fifth component consecutively exceeds the absolute value of the fifth component threshold value in the second cycle,
the third axis parameter P3 is expressed by P3=n3×N3+c3×C3+n6×N6+c6×C6,
N3 is a number of times that an absolute value of the third component exceeds an absolute value of a third component threshold value relating to the third component in the second cycle,
C3 is a maximum value of a number of times that the absolute value of the third component consecutively exceeds the absolute value of the third component threshold value in the second cycle,
N6 is a number of times that an absolute value of the sixth component exceeds an absolute value of a sixth component threshold value relating to the sixth component in the second cycle,
C6 is a maximum value of a number of times that the absolute value of the sixth component consecutively exceeds the absolute value of the sixth component threshold value in the second cycle,
coefficients n1, n2, n3, n4, n5, and n6 are one of positive or negative,
and coefficients c1, c2, c3, c4, c5, and c6 are the other of positive or negative.

8. The scratching detection system according to claim 6, wherein the first axis parameter P1 is expressed by
P1=n1×N1+c1×C1+m1×M1+n4×N4+c4×C4+m4×M4,
N1 is a number of times that an absolute value of the first component exceeds an absolute value of a first component threshold value relating to the first component in the second cycle,
C1 is a maximum value of a number of times that the absolute value of the first component consecutively exceeds the absolute value of the first component threshold value in the second cycle,
M1 is an average value of the absolute values of the first component exceeding the absolute value of the first component threshold value in the second cycles,
N4 is a number of times that an absolute value of the fourth component exceeds an absolute value of a fourth component threshold value relating to the fourth component in the second cycle,
C4 is a maximum value of a number of times that the absolute value of the fourth component consecutively exceeds the absolute value of the fourth component threshold value in the second cycle,
M4 is an average value of the absolute values of the fourth component exceeding the absolute value of the fourth component threshold value in the second cycle,
the second axis parameter P2 is expressed by P2=n2×N2+c2×C2+m2×M2+n5×N5+c5×C5+m5×M5,
N2 is a number of times that an absolute value of the second component exceeds an absolute value of a second component threshold value relating to the second component in the second cycle,
C2 is a maximum value of a number of times that the absolute value of the second component consecutively exceeds the absolute value of the second component threshold value in the second cycle,
M2 is an average value of the absolute values of the second component exceeding the absolute value of the second component threshold value in the second cycle,
N5 is a number of times that an absolute value of the fifth component exceeds an absolute value of a fifth component threshold value relating to the fifth component in the second cycle,
C5 is a maximum value of a number of times that the absolute value of the fifth component consecutively exceeds the absolute value of the fifth component threshold value in the second cycle,
M5 is an average value of the absolute values of the fifth component exceeding the absolute value of the fifth component threshold value in the second cycle,
the third axis parameter P3 is expressed by P3=n3×N3+c3×C3+m3×M3+n6×N6+c6×C6+m6×M6,
N3 is a number of times that an absolute value of the third component exceeds an absolute value of a third component threshold value relating to the third component in the second cycle,
C3 is a maximum value of a number of times that the absolute value of the third component consecutively exceeds the absolute value of the third component threshold value in the second cycle,
M3 is an average value of the absolute values of the third component exceeding the absolute value of the third component threshold value in the second cycle,
N6 is a number of times that an absolute value of the sixth component exceeds an absolute value of a sixth component threshold value relating to the sixth component in the second cycle,
C6 is a maximum value of a number of times that the absolute value of the sixth component consecutively exceeds the absolute value of the sixth component threshold value in the second cycle,
M6 is an average value of the absolute values of the sixth component exceeding the absolute value of the sixth component threshold value in the second cycles, coefficients n1, n2, n3, n4, n5, n6, m1, m2, m3, m4, m5, and m6 are one of positive or negative, and coefficients c1, c2, c3, c4, c5, and c6 are the other of positive or negative.

9. The scratching detection system according to claim 1, wherein the processor is configured to detect the existence or absence of the scratching behavior when the hand is determined to have moved based on the first signal.

10. The scratching detection system according to claim 9, wherein the detected value includes a first acceleration component along a first axis of the acceleration, a second acceleration component along a second axis of the acceleration, and a third acceleration component along a third axis of the acceleration, the second axis crosses the first axis, the third axis crosses a plane including the first and second axes, the processor determines that the hand has moved when a movement parameter exceeds an established value relating to movement, and the movement parameter is a root mean square of the first, second, and third acceleration components.

11. The scratching detection system according to claim 1, the display being further configured to display information relating to at least one of a scratching count, a scratching time, or a relative scratching time, the processor being configured to detect the existence or the absence of the scratching behavior in each of a plurality of the second cycles in an evaluation period including the plurality of second cycles, the scratching count being a number of the second cycles in which the scratching behavior is determined to exist in the evaluation period, the scratching time is a sum of the consecutive second cycles in which the scratching behavior is determined to exist in the evaluation period, and the relative scratching time is a ratio of the scratching time to the evaluation period.

\* \* \* \* \*